United States Patent
Schmit

(10) Patent No.: US 10,588,756 B2
(45) Date of Patent: Mar. 17, 2020

(54) SYSTEM AND METHOD FOR IMPLANTING AN ACETABULAR PROSTHETIC COMPONENT

(71) Applicant: DEPUY SYNTHES PRODUCTS, INC., Raynham, MA (US)

(72) Inventor: Matthew D. Schmit, Columbia City, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 334 days.

(21) Appl. No.: 15/475,753

(22) Filed: Mar. 31, 2017

(65) Prior Publication Data

US 2018/0280157 A1    Oct. 4, 2018

(51) Int. Cl.
| | | |
|---|---|---|
| A61B 17/58 | (2006.01) |
| A61B 17/60 | (2006.01) |
| A61F 2/00 | (2006.01) |
| A61F 2/46 | (2006.01) |
| A61B 17/92 | (2006.01) |
| A61F 2/34 | (2006.01) |
| A61F 2/30 | (2006.01) |

(52) U.S. Cl.
CPC ............ *A61F 2/4609* (2013.01); *A61B 17/92* (2013.01); *A61F 2/34* (2013.01); *A61F 2002/30245* (2013.01); *A61F 2002/30616* (2013.01); *A61F 2002/30822* (2013.01); *A61F 2002/4627* (2013.01); *A61F 2002/4628* (2013.01); *A61F 2002/4681* (2013.01)

(58) Field of Classification Search
CPC combination set(s) only.
See application file for complete search history.

(56) References Cited

U.S. PATENT DOCUMENTS

| | | |
|---|---|---|
| 5,108,448 A | 4/1992 | Gautier |
| 5,116,339 A | 5/1992 | Glock |
| 5,171,243 A | 12/1992 | Kashuba et al. |
| 5,417,696 A | 5/1995 | Kashuba et al. |
| 5,507,748 A | 4/1996 | Sheehan et al. |
| 5,683,399 A | 11/1997 | Jones |
| 5,928,287 A | 7/1999 | Keller |
| 5,954,727 A | 9/1999 | Collazo |
| 6,022,357 A | 2/2000 | Reu et al. |
| 6,045,583 A | 4/2000 | Gross et al. |
| 6,352,559 B1 | 3/2002 | Church |

(Continued)

FOREIGN PATENT DOCUMENTS

| | | |
|---|---|---|
| CN | 103167838 A | 6/2013 |
| DE | 19704577 A1 | 8/1998 |

(Continued)

*Primary Examiner* — Sameh R Boles
(74) *Attorney, Agent, or Firm* — Barnes & Thornburg LLP

(57) ABSTRACT

A surgical instrument for implanting an acetabular prosthetic component is disclosed, wherein the surgical instrument includes a modular head. A plurality of locking pins extends from the modular head. A locking arm extends from the modular head and is movable between an open position and a closed position. A surgical handle extends from the modular head. The modular head is removably coupled to the surgical handle. The surgical handle engages a first locking pin to lock the modular head to the surgical handle. A linkage assembly engages a second locking pin to actuate the locking arm.

14 Claims, 11 Drawing Sheets

(56) References Cited

U.S. PATENT DOCUMENTS

| | | |
|---|---|---|
| 6,468,281 B1 | 10/2002 | Badorf et al. |
| 7,037,310 B2 | 5/2006 | Murphy |
| 7,931,656 B2 | 4/2011 | Parry et al. |
| 8,277,457 B1 | 10/2012 | Burgi et al. |
| 8,535,324 B2 | 9/2013 | Aux Epaules et al. |
| 8,956,366 B2 | 2/2015 | Aux Epaules et al. |
| 9,028,502 B2 * | 5/2015 | Burgi .................... A61F 2/4609 606/91 |
| 10,405,991 B2 | 9/2019 | Bailey |
| 2004/0215200 A1 | 10/2004 | Tomier et al. |
| 2005/0137603 A1 | 6/2005 | Belew et al. |
| 2005/0149047 A1 | 7/2005 | Parry et al. |
| 2005/0209597 A1 | 9/2005 | Long et al. |
| 2005/0228394 A1 | 10/2005 | Bihary et al. |
| 2006/0149285 A1 | 7/2006 | Burgi et al. |
| 2006/0167462 A1 | 7/2006 | Raugel et al. |
| 2006/0229630 A1 | 10/2006 | Collins et al. |
| 2009/0234453 A1 | 9/2009 | Steinberg |
| 2009/0248027 A1 | 10/2009 | Imhof et al. |
| 2009/0281550 A1 | 11/2009 | Keller |
| 2011/0288649 A1 | 11/2011 | Ratzel et al. |
| 2011/0301654 A1 | 12/2011 | Wozencroft et al. |
| 2012/0029524 A1 | 2/2012 | Imhof-Rothlin et al. |
| 2012/0059383 A1 | 3/2012 | Murphy et al. |
| 2013/0079785 A1 | 3/2013 | Burgi |
| 2015/0094728 A1 | 4/2015 | Rhoades et al. |
| 2016/0228262 A1 | 8/2016 | Bailey |
| 2017/0020687 A1 | 1/2017 | Rhoades et al. |
| 2019/0231558 A1 | 8/2019 | Beck et al. |

FOREIGN PATENT DOCUMENTS

| | | |
|---|---|---|
| DE | 19722923 A1 | 8/1998 |
| DE | 10128234 A1 | 1/2003 |
| DE | 10250390 A1 | 5/2004 |
| DE | 102008049661 A1 | 4/2010 |
| EP | 0811360 A2 | 12/1997 |
| EP | 2347736 A1 | 7/2011 |
| FR | 2797180 A1 | 2/2001 |
| FR | 2809305 A1 | 11/2001 |
| FR | 2877210 A1 | 5/2006 |
| FR | 2917288 A1 | 12/2008 |
| GB | 2299758 A | 10/1996 |
| GB | 2473610 A | 3/2011 |
| WO | 2008099242 A1 | 8/2008 |

\* cited by examiner

SYSTEM AND METHOD FOR IMPLANTING AN ACETABULAR PROSTHETIC COMPONENT

BACKGROUND

The present disclosure relates to surgical instruments, and, more specifically, to designs for an acetabular prosthetic component and an instrument for implanting an acetabular prosthetic component such as, for example, an acetabular cup.

TECHNICAL FIELD

Orthopaedic implants or prostheses are implanted in patients by orthopaedic surgeons to, for example, correct or otherwise alleviate bone and/or soft tissue loss, trauma damage, and/or deformation of the bone(s) of the patients. One orthopaedic surgical procedure in which an orthopaedic implant is used is a partial or total hip replacement procedure. One of the implant components used in such a surgical procedure is an acetabular prosthetic component such as, for example, an acetabular cup, which is secured to the acetabulum of the patient. The acetabular cup replaces the natural bearing surface of the acetabulum and provides a new bearing surface for the head portion of the patient's femur or femoral implant component.

Generally, during a hip implant procedure, an acetabular cup may be implanted into the pelvis of a patient. The acetabular cup is typically positioned on an end of a surgical instrument that is utilized during surgery to implant the acetabular cup into an acetabular cavity of the pelvis. The acetabular cup often includes a threaded end that is threaded to the end of the surgical instrument. The surgical instrument is then inserted into the surgical site so that the acetabular cup is positioned proximate to the acetabular cavity. While holding the surgical instrument in place with the acetabular cup aligned with the acetabular cavity, the surgeon may apply force to an end of the surgical instrument opposite the acetabular cup. For example, the surgeon may utilize a mallet to apply force to an end of the surgical instrument that is distal from the patient and the surgical site. The force drives the acetabular cup into position within the acetabular cavity, where a frictional surface of the acetabular cup engages the bone of the acetabular cavity to retain the acetabular cup therein.

SUMMARY

According to one aspect of the disclosure, an orthopaedic surgical instrument assembly is disclosed. A distal end of the surgical instrument provides a handle during surgery. The instrument assembly also includes a modular head that is removably coupled to a surgical handle. The surgical handle includes a locking mechanism that removably secures the modular head to the handle and a locking mechanism that secures an acetabular prosthetic component such as, for example, an acetabular cup, to the modular head. The locking mechanism may be actuated between the locked position and an unlocked position to free the acetabular prosthetic component from the modular head.

According to another aspect, a surgical instrument for implanting an acetabular prosthetic component is disclosed, wherein the surgical instrument includes a modular head having a proximal end to retain the acetabular prosthetic component and an opposite distal end. A plurality of locking pins extends from the distal end of the modular head. A cap is positioned at the proximal end of the modular head. The cap includes a cap surface. A locking arm extends from the proximal end of the modular head. The locking arm is movable between an open position and a closed position. The locking arm is positioned adjacent the cap. In the open position the locking arm is spaced further from the cap than in the closed position. A surgical handle extends distally from the modular head. The modular head is removably coupled to a proximal end of the surgical handle. The surgical handle includes a user-operated button having a body that engages a first of the plurality of locking pins of the modular head to lock the modular head to the surgical handle. A linkage assembly engages a second of the plurality of locking pins to actuate the locking arm.

In some embodiments, the cap includes a hemi-spherical outer surface sized to receive a hemi-spherical concave surface of the acetabular prosthetic component. A circular rim extends circumferentially around a distal end of the cap. The locking arm includes a locking flange extending toward the hemi-spherical outer surface. The locking flange engages a groove of the acetabular prosthetic component when the locking arm is in the closed position.

In some embodiments, each of the plurality of locking pins includes a groove formed therein. The body of the user-operated button includes a bracket that engages the groove formed in the first of the plurality of locking pins. The user-operated button may translate from a first side of the surgical handle toward a second side of the surgical handle to disengage the bracket of the body from the groove of the first of the plurality of locking pins to facilitate removing the modular head from the surgical handle. The linkage assembly may include an attachment link having a mounting leg. The mounting leg of the attachment link engages the groove of the second of the plurality of locking pins. The user-operated button may translate from a first side of the surgical handle toward a second side of the surgical handle to pivot the attachment link so that the mounting leg of the attachment link disengages the groove of the second of the plurality of locking pins to facilitate removing the modular head from the surgical handle.

According to a further aspect, a surgical instrument for implanting an acetabular prosthetic component having a modular head is disclosed. The modular head includes a proximal end to retain the acetabular prosthetic component and an opposite distal end. A hemi-spherical outer surface is positioned at the proximal end and is sized to receive a hemi-spherical concave surface of the acetabular prosthetic component. A circular rim extends circumferentially around a distal end of the hemi-spherical outer surface. A stationary pin and a moveable pin extend from the distal end of the modular head. A locking arm extends from the proximal end of the modular head and is hingedly coupled to the moveable pin. The moveable pin is moveable linearly in a first direction and a second direction to pivot the locking arm between an open position and a closed position. In the open position the locking arm is spaced further from the hemi-spherical outer surface than in the closed position.

In some embodiments, the surgical instrument also includes a surgical handle extending distally from the modular head. The modular head is removably coupled to a proximal end of the surgical handle. The surgical handle includes a user-operated button having a body that engages the stationary pin of the modular head to lock the modular head to the surgical handle. A linkage assembly engages the moveable pin to actuate the locking arm. The linkage assembly extends a length of the surgical handle from the proximal end of the surgical handle to a distal end of the surgical handle. The linkage assembly includes a lever at the distal end of the surgical handle. The lever is actuated to move the locking arm.

In some embodiments, the lever is actuated from a locked positioned to an unlocked position. In the locked positioned the attachment link is translated distally to move the moveable pin distally. In the unlocked position the attachment link is translated proximally to move the moveable pin proximally. Moving the moveable pin distally actuates the locking arm into the closed position, and moving the moveable pin proximally actuates the locking arm into the open position. A lever release may retain the lever in the locked position. The lever release is actuated to release the lever into the unlocked position. The lever is positioned on a bottom of the surgical handle and rotates therefrom. The lever release is positioned on a top of the surgical handle and translates distally and proximally along a length of the surgical handle. Translating the lever release distally releases the lever into the unlocked position. Positioning the lever in the locked position locks the user-operated button to lock the modular head to the surgical handle.

According to yet another aspect, a surgical handle that is removably coupled to a modular head for implanting an acetabular prosthetic component is disclosed, wherein the surgical handle includes a user-operated button having a body that engages a stationary pin of the modular head to lock the modular head to a proximal end of the surgical handle. A linkage assembly engages a moveable pin of the modular head to actuate a locking arm of the modular head. The linkage assembly extends a length of the surgical handle from the proximal end of the surgical handle to a distal end of the surgical handle. The linkage assembly includes a lever at the distal end of the surgical handle. The lever is actuated to move the locking arm of the modular head.

BRIEF DESCRIPTION OF THE DRAWINGS

The foregoing and other features of the various embodiments of the methods and apparatuses described herein will become more apparent from the following detailed description and the accompanying drawings in which.

DETAILED DESCRIPTION OF THE DRAWINGS

Figure 1:
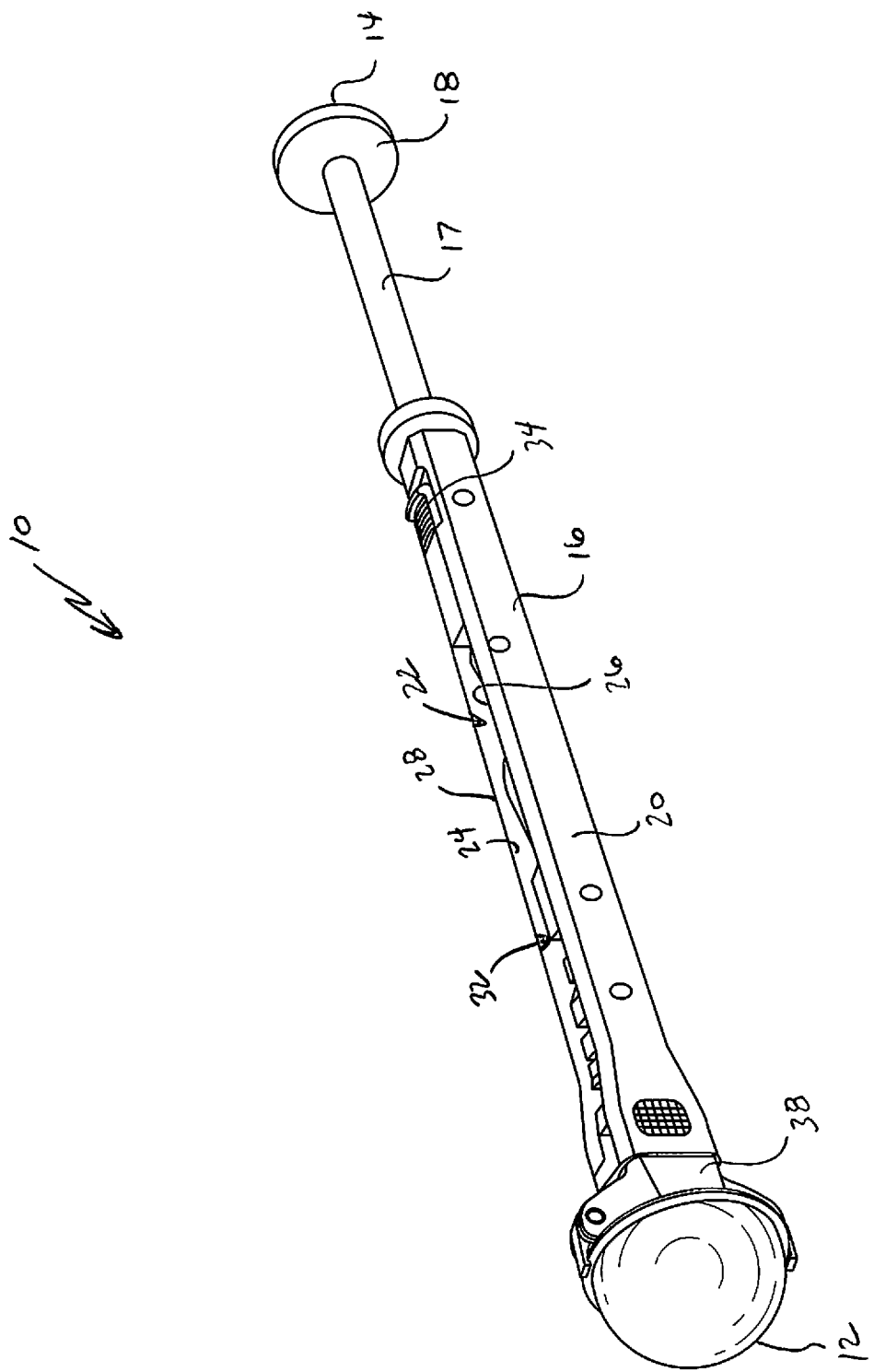
FIG. 1 is a perspective view of one embodiment of a surgical instrument assembly for implanting an acetabular prosthetic component.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, a surgical instrument assembly 10 for implanting an acetabular prosthetic component 40 (see FIG. 2) is shown. In the illustrative embodiment, the assembly 10 includes a handle 16 and a modular head 38 that is removably coupled to a proximal end of the handle 16. As described in greater detail below, the modular head 38 defines the proximal end 12 of the assembly 10 and is configured to be attached to the acetabular prosthetic component 40 and positioned in the acetabular cavity of a patient during a surgical procedure.

The handle 16 extends to a distal end 14 that includes a grip 17 sized to be grasped by a surgeon to grip during use and an impaction plate 18 for applying force to the surgical instrument assembly 10 (and hence the component 40) during surgery. The handle 16 also includes a linkage housing 20 that extends proximally from the grip 17. The linkage housing 20 has a cavity 22 extending therethrough that is defined between a first sidewall 24 and a second sidewall 26. The cavity 22 extends through the linkage housing 20 from a top opening 28 to a bottom opening 30 (see FIG. 7), and the handle 16 includes a linkage assembly 32 that is positioned in the cavity 22. As described in greater detail below, the linkage assembly 32 is operable to secure the acetabular prosthetic component 40 to the modular head 38 and the modular head 38 to the handle 16. As shown in FIG. 1, the handle 16 also includes a lever release 34, which is coupled to the linkage assembly 32 at the distal end of the linkage housing 20. The lever release 34 may be actuated to release the lever to move between an extended position (see FIG. 14) in which the acetabular prosthetic component 40 may be detached from the modular head 38 and a retracted position (see FIG. 7) within the cavity 22 formed in the linkage housing 20. In the retracted position, the acetabular prosthetic component 40 is secured to the modular head 38.

Figure 2:
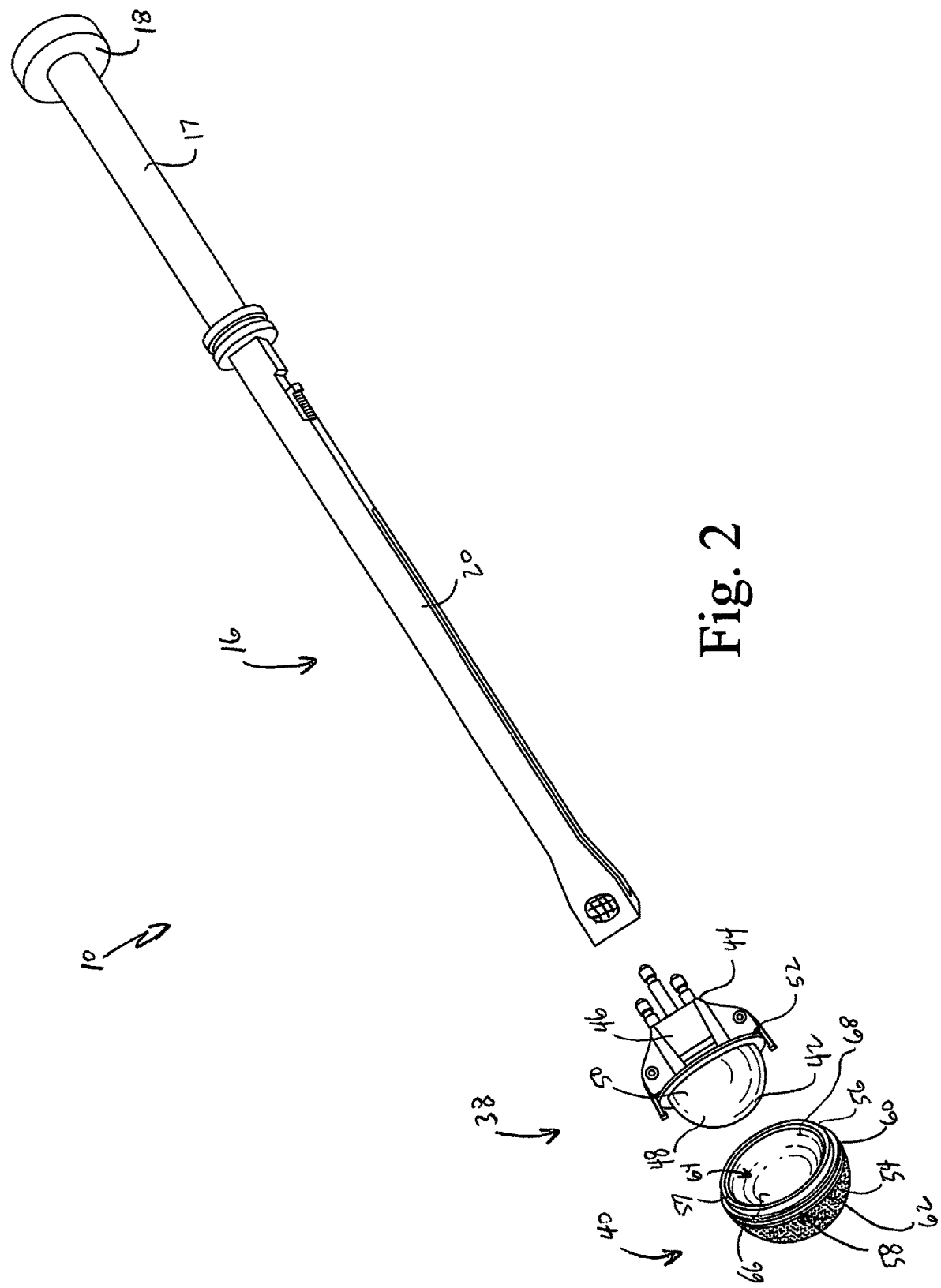
FIG. 2 is an exploded view of the surgical instrument assembly of FIG. 1 and the acetabular prosthetic component.

Referring now to FIG. 2, the modular head 38 extends from a proximal end 42 and a distal end 44. The proximal end 42 is configured to receive the acetabular prosthetic component 40 thereon, and the distal end 44 is configured to be removably coupled to the linkage housing 20. In the illustrative embodiment, the distal end 44 includes a body 46 that is configured to be removably coupled to the linkage housing 20, and a cap 48 is positioned at the opposite proximal end 42. The cap 48 has a cap surface 50 that is generally formed as a hemi-spherical dome or a convex dome and a rim 52 extending circumferentially around a distal end of the cap 48. The cap 48 is sized to receive the acetabular prosthetic component 40, as described in greater detail below. In one embodiment, the cap 48 is formed from a different material than the rest of the surgical instrument 10. For example, the cap 48 may be formed from a polymer to reduce an amount of stress on the acetabular prosthetic component 40 during implantation.

Referring to FIG. 2, the acetabular prosthetic component 40 includes a convex hemi-spherical outer surface 54 that is sized to be received in an acetabular cavity of the patient. In one embodiment, the surface 54 is a porous surface that promotes bone growth within the acetabular cavity. A distal end 56 of the acetabular prosthetic component 40 includes a circular end surface 57 and a groove 58 formed circumferentially around of the distal end 56. The groove 58 is defined between a proximal sidewall 60 and a distal sidewall 62.

The component 40 also includes a concave hemi-spherical cavity that is formed opposite the outer surface 54. A polymer insert 66 is positioned in the cavity and has a concave hemi-spherical surface 68 that defines an insert cavity 64. In the illustrative embodiment, the hemi-spherical cap surface 50 of the modular head 38 is sized and shaped to match the concave hemi-spherical surface 68 of the polymer insert 66 such that the cap 48 of the modular head 38 is configured to be received within the insert cavity 64.

It should be appreciated that in some embodiments the instrument assembly 10 may be included an orthopaedic prosthesis system that includes multiple sizes of acetabular prosthetic components. In such embodiments, the instrument assembly 10 may include a plurality of modular heads 38 that are configured to be separately coupled to the handle 16. Each modular head 38 may include a cap 48 that may be sized for a particular size acetabular prosthetic component 40. The surgeon may change the modular head 38 of the surgical instrument 10 during surgery dependent on a size of the acetabular prosthetic component 40 to be implanted.

Figure 4:
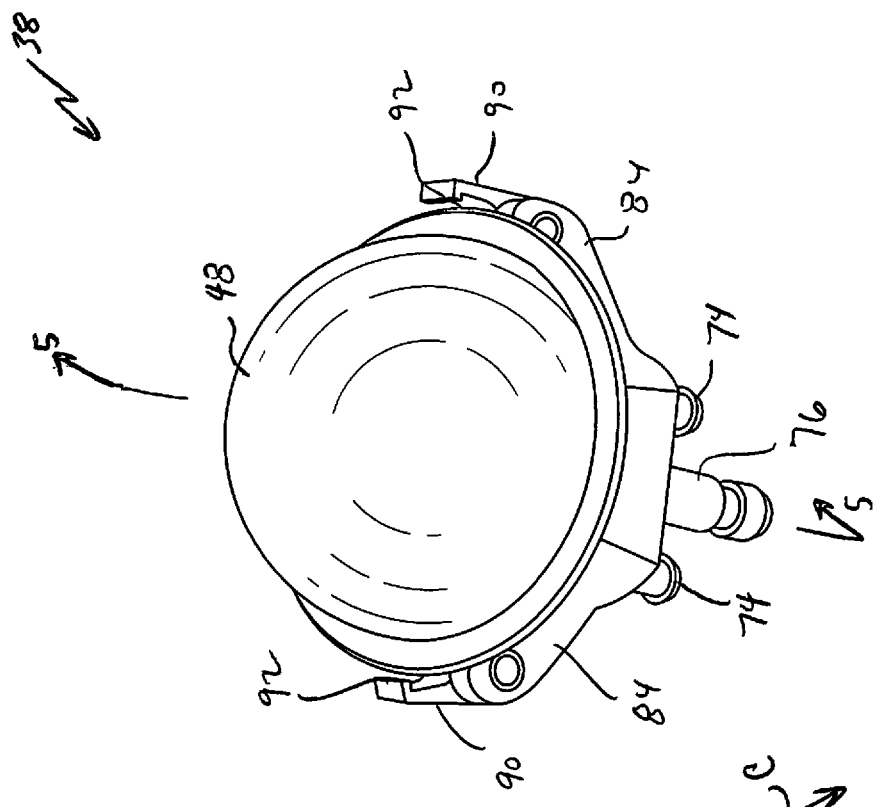
FIG. 4 is another perspective view of the modular head component of FIG. 3.
Figure 3:
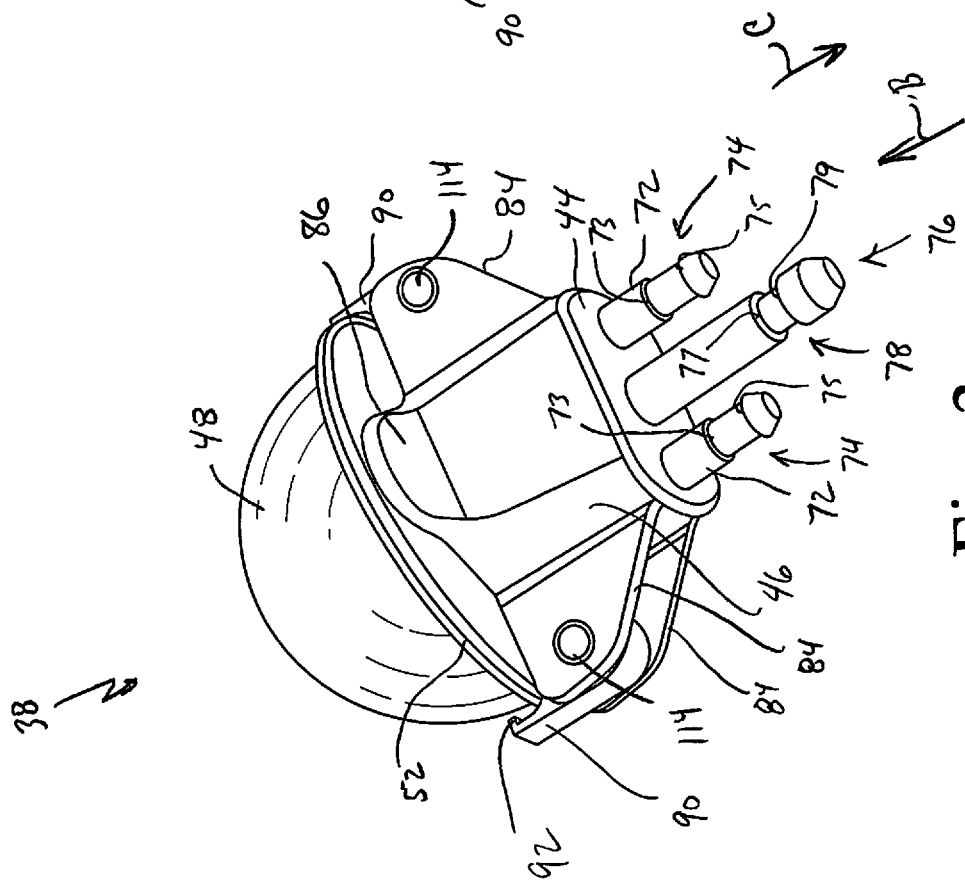
FIG. 3 is a perspective view of a modular head component of the surgical instrument assembly of FIG. 1.

Referring now to FIGS. 3-4, the modular head 38 includes a body 46 that is configured to be removably coupled to the linkage housing 20 and the cap 48, which is secured to the body 46. The modular head 38 includes a number of flanges 84 that extend from opposite sides of the body 46. Another pair of flanges 86 extends outwardly from the body 46 between the flanges 84. The flanges 84 and 86 cooperate to provide support for the rim 52 of the cap 48.

The modular head 38 also includes a pair of stationary pins 72 that are engaged by the linkage assembly 32 to secure the head 38 to the handle 16. As shown in FIGS. 3-4, the pins 72 extend from the distal end 44 of the body 46. The stationary pins 72 are formed integrally with the body 46 of the modular head 38 in the illustrative embodiment. In other embodiments, the pins may be formed separately from the body 46. A groove 74 is formed around a circumference of each pin 72 between a proximal sidewall 73 and a distal sidewall 75. Each groove 74 is sized to receive flanges 260 (FIG. 10) of the linkage assembly 32 to secure the head 38 to the handle 16, as described in greater detail below.

The modular head 38 also includes a moveable pin 76 that is actuated by the linkage assembly 32 to secure the prosthetic component 40 to the modular head 38. The moveable pin 76 also extends outwardly from the distal end 44 of the body 46, as shown in FIGS. 3-4. The moveable pin 76 includes a groove 78 that is defined by a proximal sidewall 77 and a distal sidewall 79. When actuated by the linkage assembly 32, the moveable pin 76 is configured to move in the directions indicated by arrows B and C to move the groove 78 toward and away from the distal end 44 of the body 46.

The modular head 38 also includes a pair of locking arms 90 that are connected to the moveable pin 76. In the illustrative embodiment, the locking arms 90 are actuated by the movement of the pin 76 to secure the prosthetic component 40 to the modular head 38. As shown in FIGS. 3-4, each locking arm 90 includes a locking flange 92 that extends inwardly toward the cap 48. When moved to a closed position by the movement of the pin 76 (described in more detail below), the locking flange 92 is positioned within the groove 58 formed in the acetabular prosthetic component 40. In such a position, the locking flange 92 is secured against the distal sidewall 62 forming the groove 58 so that the engagement between the distal sidewall 62 and the locking flange 92 prevents the acetabular prosthetic component 40 from being removed from the cap 48 of the modular head 38. When moved to an open position by the movement of the pin 76 (described in more detail below), the locking flange 92 is spaced apart from the distal sidewall 62 and removed from the groove 58 of the acetabular prosthetic component 40 such that the acetabular prosthetic component 40 may be removed from the cap 48 of the modular head 38.

Figure 5:
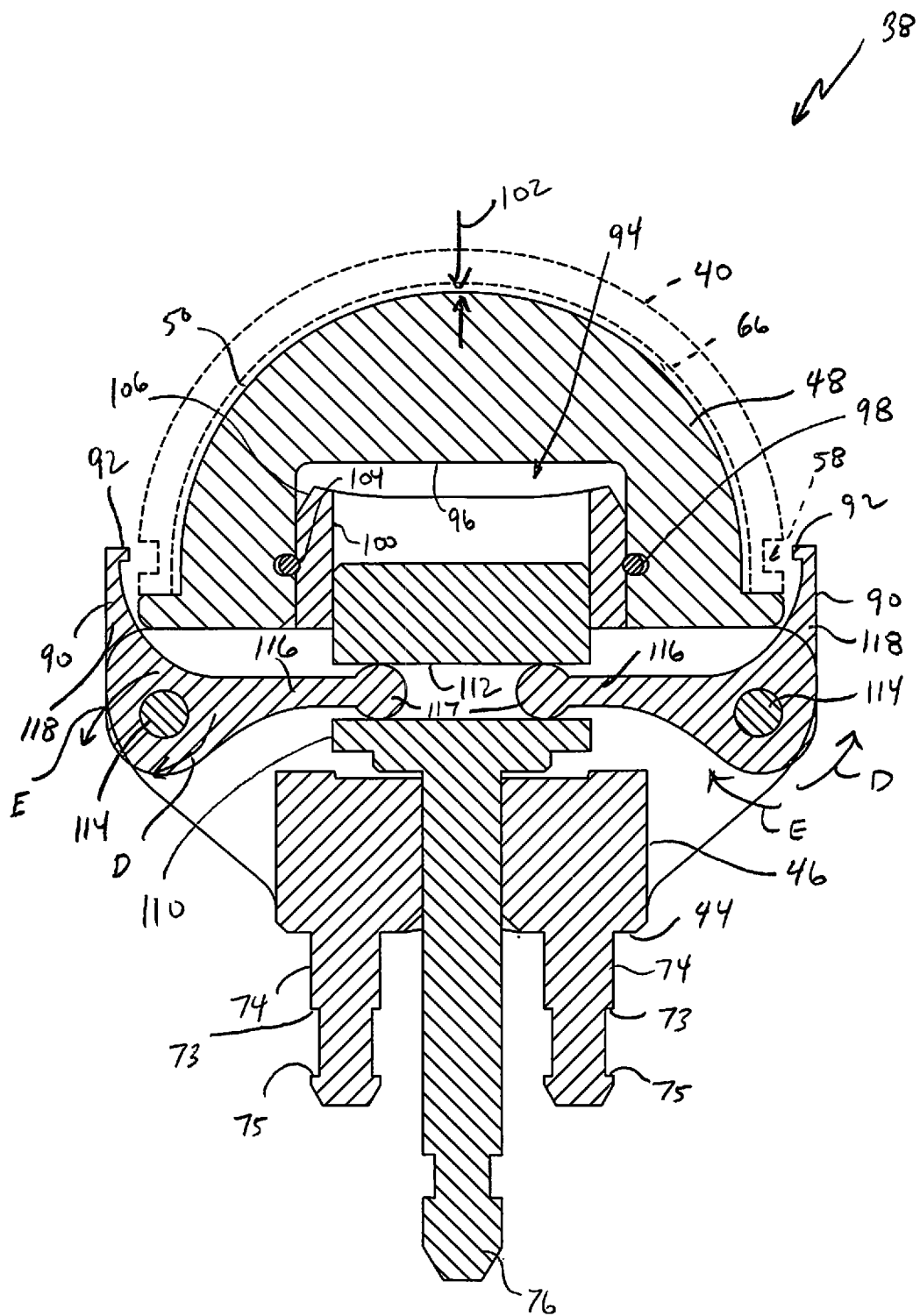
FIG. 5 is a cross-sectional view of the modular head component taken along the line A-A in FIG. 3.

Referring now to FIG. 5, each locking arm 90 is attached to a plug 110 attached to the proximal end of the moveable pin 76. A passageway 112 extends through the plug 110 and receives a portion of the locking arms 90 therein. In the illustrative embodiment, each locking arm 90 is formed in a substantially "L-shape" configuration and is mounted on a pivot pin 114 secured to each flange 86. A first end 116 and a second end 118 of the locking arms 90 extend away the pivot pin 114. The first end 116 of the locking arm 90 is positioned within the passageway 112 of the plug 110. The first end 116 of each locking arm 90 has a substantially circular end pin 117 such that the first end 116 of each locking arm 90 may rotate within the passageway 112.

The second end 118 of each locking arm 90 extends proximally toward the cap 48 and includes the locking flange 92 of the arm 90. As shown in FIG. 5, the first end 116 and the second end 118 extend substantially 90 degrees with respect to one another. The locking arm 90 rotates or pivots as indicated by arrows D-E about the pivot pin 114 between the open position shown in FIG. 5 and the closed position described above.

The plug 110 of the moveable pin 76 extends through the body 46 and is received in a passageway defined in a mounting shaft 100 of the modular head 38. As shown in FIG. 5, the mounting shaft 100 is sized to receive the cap 48, which, as described above, is configured to receive the prosthetic component 70. In the illustrative embodiment, a cavity 94 is defined in the cap 48 by an inner surface 96 opposite the cap surface 50. The modular head 38 also includes a retaining ring 98 that is secured in an annular groove defined in the inner surface 96. The mounting shaft 100 includes a groove 104 formed circumferentially in the outer surface 106 of the mounting shaft 100. The retaining ring 98 of the cap 48 is received within the groove 104 of the shaft 100 to secure the cap 48 to modular head body 46.

When actuated by the linkage assembly 32, the moveable pin 76 is moved linearly in the proximal direction of arrow B, thereby causing the locking arm 90 to pivot such that the second end 118 of the locking arm 90 pivots away from the cap 48 in the direction of arrow D to the open position. In the open position, the acetabular prosthetic component 40 may be positioned on the cap 48 such that the rim surface 70 engages the end surface 57 of the acetabular prosthetic component 40.

When moving to the closed position by the linkage assembly 32, the moveable pin 76 is moved linearly in the distal direction of arrow C, thereby causing the locking arm 90 to pivot such that the second end 118 of the locking arm 90 pivots toward the cap 48 in the direction of arrow E. In the closed position, the locking flange 92 is secured within the groove 58 of the acetabular prosthetic component 40 by engaging the distal sidewall 62 of the groove 58. The locking flange 92 locks the acetabular prosthetic component 40 to the modular head 38 in the closed position. As described below, the moveable pin 76 is translated in the direction of arrows B and C by actuation of the linkage assembly 32.

As shown in FIG. 5, the acetabular prosthetic component 40 is positioned on the cap 48 such that a gap 102 is provided between the cap surface 50 and the insert cavity 64 of the acetabular prosthetic component 40. By providing the gap 102 between the cap surface 50 and the insert cavity 64, force may be prohibited from being transmitted to the insert cavity 64 of the acetabular prosthetic component 40 during implantation. The rim 52 includes a rim surface 70 that faces proximally from the body 46 of the modular head 38 and is configured to engage the end surface 57 of the acetabular prosthetic component 40. By providing engagement between the rim surface 70 and the end surface 57 of the acetabular prosthetic component 40, force may be transmitted through the end surface 57 of the acetabular prosthetic component 40 during implantation.

Figure 6:
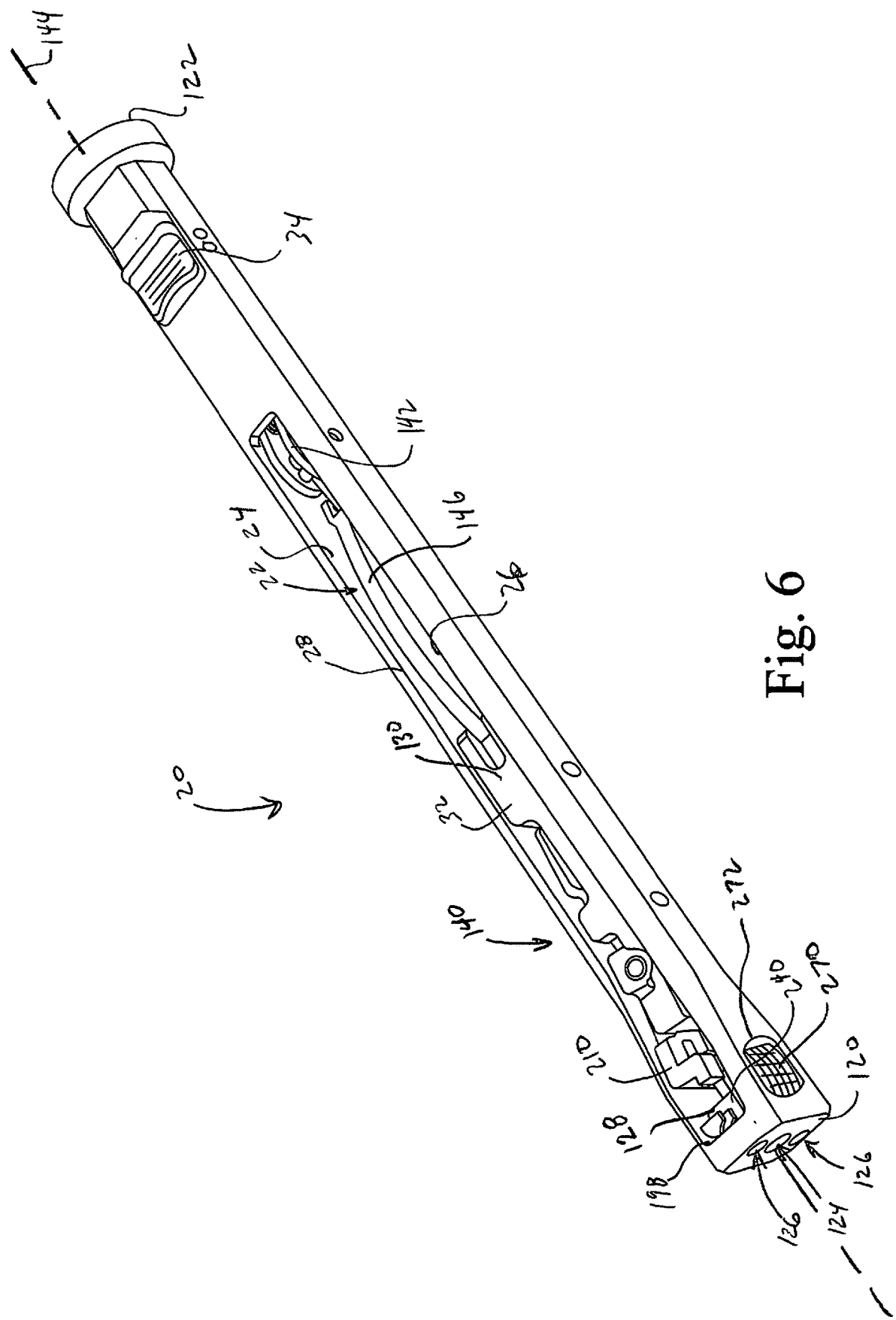
FIG. 6 is a perspective view of the linkage housing of the surgical instrument of FIG. 1.
Figure 7:
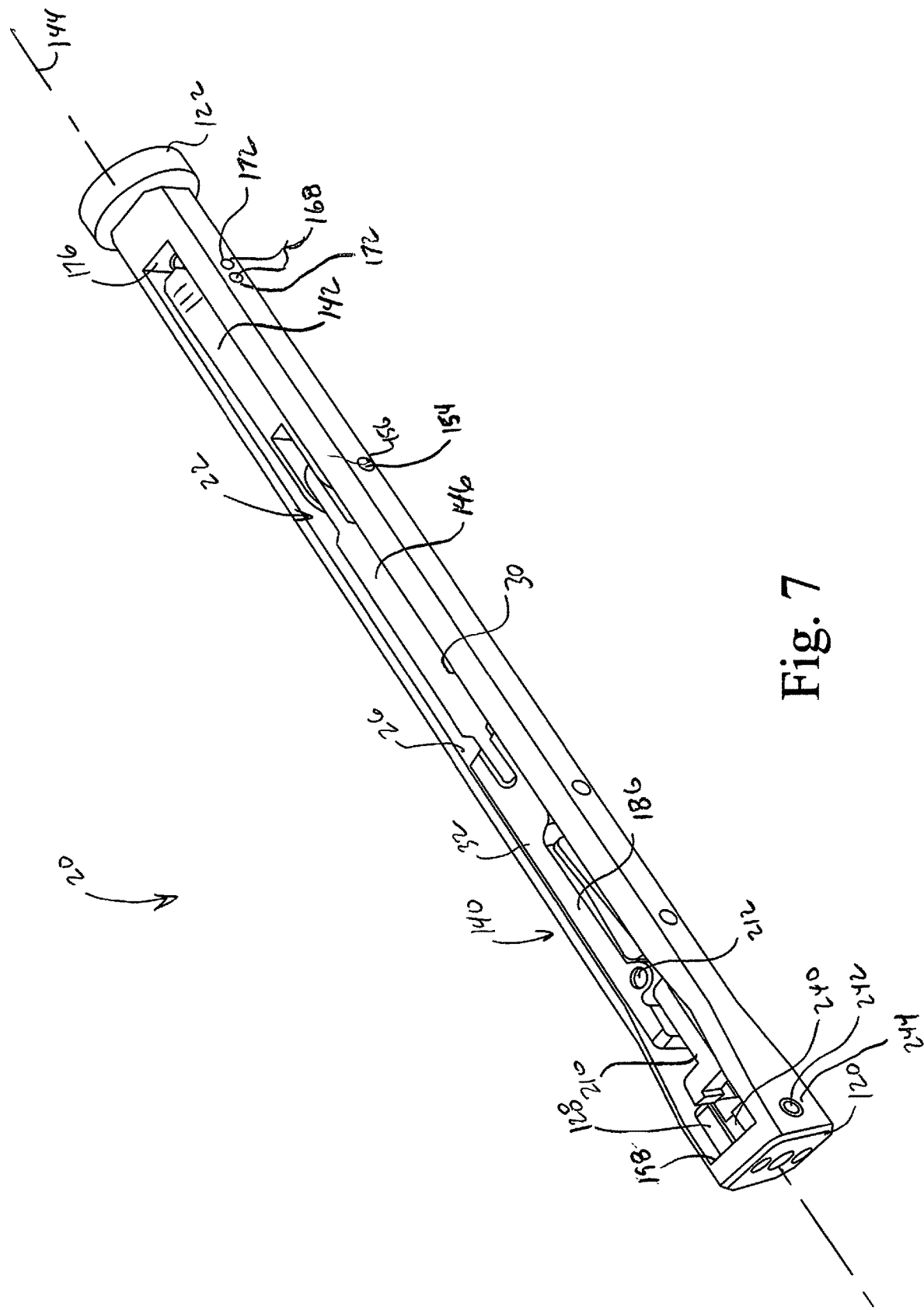
FIG. 7 is another perspective view of the linkage housing of FIG. 6 showing the opposite side of the linkage housing.

Referring now to FIGS. 6 and 7, the linkage housing 20 extends from a proximal end 120 configured to be secured to the modular head 38 to an opposite distal end 122 attached to the grip 17. The proximal end 120 includes an aperture 124 and a pair of apertures 126 extending through the sidewall of the linkage housing 20 into the cavity 22. The apertures 126 receive the stationary pins 72, and the aperture 124 receives the moveable pin 76 so that the stationary pins 72 and the moveable pin 76 extend into the cavity 22 to be coupled to the linkage assembly 32.

In the illustrative embodiment, the linkage assembly 32 is operable to secure and release the modular head 38 from the handle 16. The linkage assembly 32 is also operable to secure and release an acetabular prosthetic component 40 from the modular head 38 when the modular head is secured to the handle 16. It should be appreciated that in other embodiments the surgical instrument assembly 10 may include separate linkage assemblies that are operable to perform those separate functions. To secure the modular head 38 to the handle 16, the leakage assembly 32 includes a modular head locking 128 that is positioned at the proximal end 120 of the linkage housing 20 and is configured to engage the stationary pins 72 of the modular head 38. To secure the acetabular prosthetic component 40 to the modular head 38, the linkage assembly 32 includes a prosthetic component locking mechanism 130 that engages the movable pin 76 of the modular head 38. As described in greater detail below, the modular head locking mechanism 128 includes various components of the prosthetic component locking mechanism 130.

As shown in FIG. 7, the component locking mechanism 130 includes a proximal assembly 140 that is positioned in the cavity 22 and a control lever 142 that is pivotally coupled to the housing 20. The proximal assembly 140, which is configured to be coupled to the movable pin 76 of the modular head 38, is operable to move proximally and distally along the longitudinal axis 144 of the housing 20. In the illustrative embodiment, connecting linkage 146 couples the control lever 142 to the proximal assembly 140 such that as the control lever 142 is pivoted between the closed position shown in FIG. 7 and the open position shown in FIG. 14, the proximal assembly 140 is advanced proximally along the cavity 22 toward the proximal end 120 of the housing 20. When the control lever is pivoted from the open position back to the closed position, the proximal assembly 140 is advanced distally away from the proximal end 120 of the housing 20.

Figure 8:
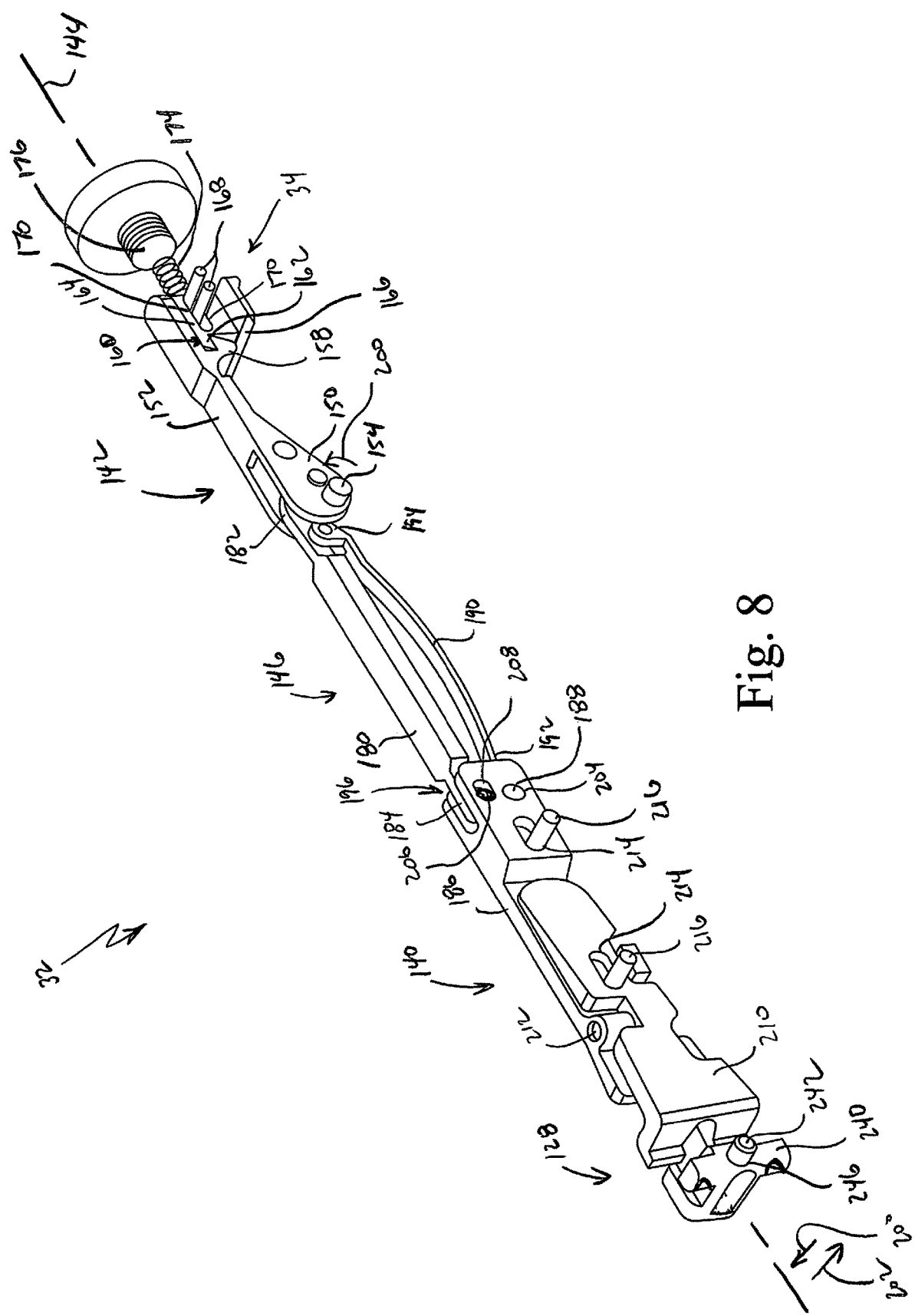
FIGS. 8-10 are perspective views of the linkage assembly of the surgical instrument of FIG. 1.

Referring now to FIG. 8, the control lever 142 includes a base 150 and an arm 152 that extends distally from the base 150. The base 150 is coupled to the housing 20 via a pivot pin 154 that is received in a bore 156 (see FIG. 7). The control lever 142 also includes a locking tab 158 that extends from the arm 152. In the illustrative embodiment, the locking tab 158 includes a channel 160 that receives a flange 162 of the lever release 34 to retain the control lever 142 in the closed position.

As described above, the lever release 34 may be operated to release the control lever 142 from the closed position. As shown in FIG. 8, the lever release 34 includes a body 164 that is positioned in the cavity 22 of the housing 20. The body 164 extends outwardly through the housing 20 and is connected to a user-operated button 166 that is positioned on the outer surface of the housing 20. The body 164 is mounted to the housing 20 via a pair of pins 168, which extend through an elongated slot 170 defined in the body 164 and are received in bores 172 defined in the housing 20 (see FIG. 7). The elongated slot 170 extends along the axis 144 of the housing 20, and interaction between the pins 160 and slot 170 guide the longitudinal movement of the lever release 34 relative to the housing 20. The flange 162 of the locking tab 158 extends proximally from the body 164, as shown in FIG. 8.

The locking mechanism 130 includes a biasing element 174 that is positioned between the body 164 of the lever release 34 and the distal inner wall 176 of the housing 20. In the illustrative embodiment, the biasing element 174 is a helical spring that biases the lever release 34 in a proximal direction and into engagement with the locking tab 158 when the control lever 142 is in the closed position shown in FIG. 8.

As described above, a connecting linkage 146 extends between the control lever 142 and the proximal assembly 140 of the component locking mechanism 130. In the illustrative embodiment, the connecting linkage 146 includes a main link 180 that has a distal end 182 that is positioned in a channel defined in the base 150 of the control lever 142. The main link distal end 182 is pivotally coupled to the base 150, and the opposite end 184 of the main link 180 is coupled to a base link 186 of the proximal assembly 140 within a channel 196 defined in the base link. The connecting linkage 146 also includes a leaf spring 190 that is coupled at its proximal end 192 to the base link 186 within the channel 196 and is coupled at its distal end 194 to the distal end 182 of the main link 180.

Figure 9:
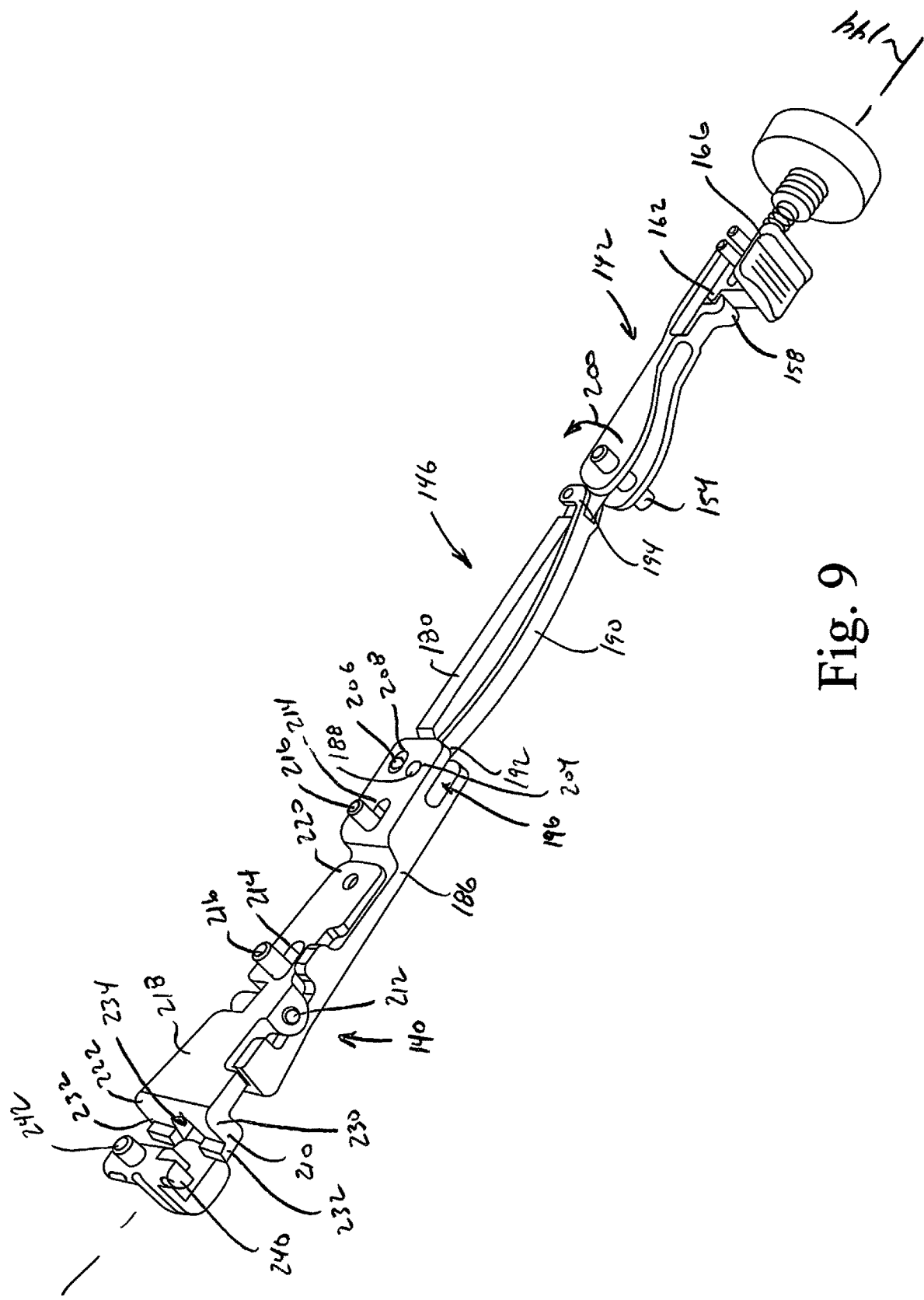

In the illustrative embodiment, the distal end 182 of the main link 180 is offset from the pivot pin 154 that couples the control lever 142 to the housing 20. When the control lever 142 moves from the closed position to the open position, the distal end 182 of the main link 180 pivots about the pin 154 with the arm 152 of the control lever 142 as indicated by arrow 200 in FIG. 8. As the distal end 182 pivots about the pin 154, the tension on the leaf spring 190 is relieved as its ends 192, 194 are moved closer together. As shown in FIGS. 8-9, the proximal end 192 of the leaf spring 190 is pivotally coupled to the base link 186 via a pin 188 that extends through bores 204 defined in the link 186 and spring 190. The proximal end 184 of the main link 180 is also pivotally coupled to the base link 186. However, the main link 180 is connected to the base link 186 via a pin 206 that is positioned an elongated slot 208 defined in the base link 186. As a result, the main link 180 is configured to slide longitudinally along the axis 144 of the housing 20 relative to the base link 186.

The proximal assembly 140 includes the base link 186 and an attachment link 210 that is configured to engage the movable pin 76 of the modular head 38. In the illustrative embodiment, the attachment link 210 is pivotally coupled to the base link via a pin 212 that extends transverse to the longitudinal axis 144 of the housing 20. The base link 186 includes a pair of elongated slots 214 that receive pins 216, 236 to couple the base link 186 to the housing 20. The attachment link 210 also includes an elongated slot 214 that receives the pin 236 to couple the attachment link to the housing 20. In the illustrative embodiment, the pin 236 includes a stepped wall 238 (see FIG. 11) that is configured to engage a corresponding wall 248 of the attachment link 210, as described in greater detail below.

As shown in FIGS. 8-9, the attachment link 210 has an elongated body 218 that extends from a distal end 220 to a proximal end 222. A mounting bracket 230 extends away from the proximal end of the elongated body 218 of the attachment link 210. In the illustrative embodiment, the mounting bracket 230 includes a pair of legs 232 that extends transverse to the longitudinal axis 144 of the housing 20. A slot 234 is defined between the legs 232. The slot 234 is sized to be positioned over the distal end of the movable pin 76 of the modular head 38 so that the legs 232 are positioned in the groove 78 of the movable pin 76.

As described above, the linkage assembly 32 also includes a modular head locking mechanism 128 that is configured to secure a modular head 38 to the handle 16. In the illustrative embodiment, the locking mechanism 128 includes a bracket 240 that is positioned between the attachment link 210 of the prosthetic component locking mechanism 130 and the proximal inner wall 198 of the housing 20, as shown in FIGS. 6-7. The bracket 240 is coupled to the housing 20 via a pin 242 that is positioned and a bore 244 defined in the housing 20. As shown in FIGS. 8-9, the pin 242 extends transverse to the longitudinal axis 144 of the housing 20 into an aperture 246 defined in the bracket 240. The aperture 246 is sized so that the bracket 240 is operable to be moved relative to the housing 20 in the directions indicated by arrows 250, 252.

Figure 10:
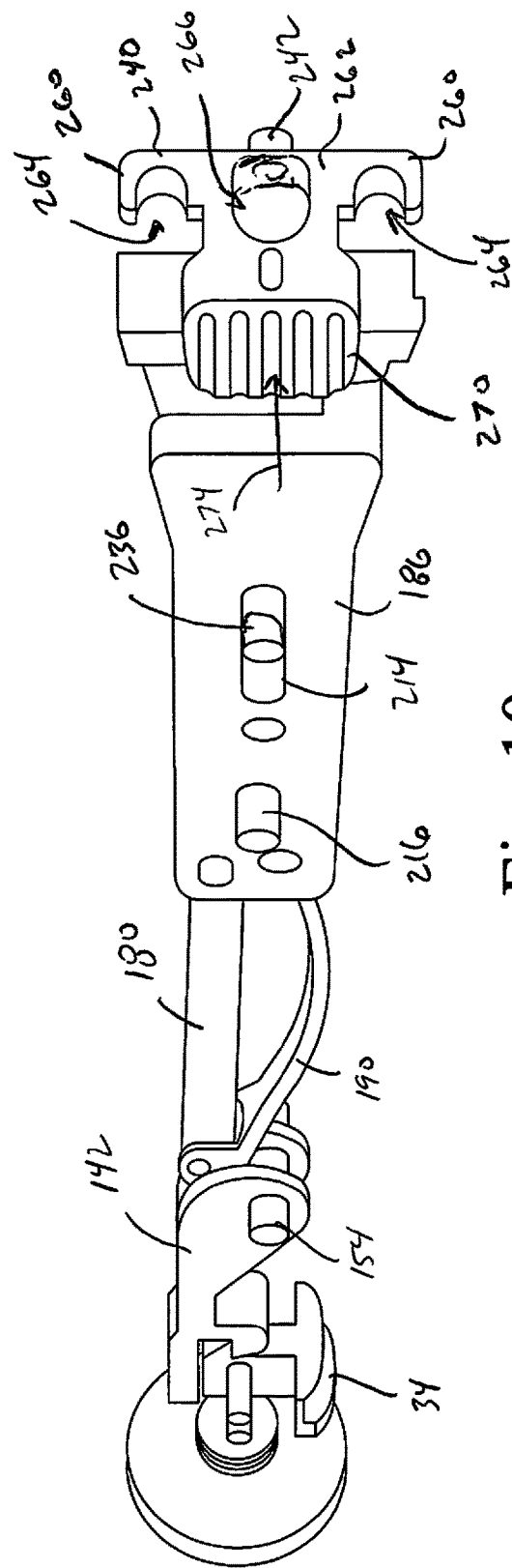

Referring now to FIG. 10, the bracket 240 includes a pair of flanges 260 that extend outwardly from a central body 262. Each of the flanges 260 has a slot 264 defined therein that is sized to receive one of the stationary pins 72 of the modular head 38. The central body 262 has an elongated slot 266 that is sized such that the movable pin 76 of the modular head 38 extends through the center body 262 to engage the attachment link 210. The bracket 240 also includes a user-operated button 270 that is positioned in an opening 272 defined in the housing 20. As described in greater detail below, when a user presses the button 270 in the direction indicated by arrow 274 in FIG. 10, the locking mechanism 128 is actuated to receive or release the modular head 38.

Figure 11:
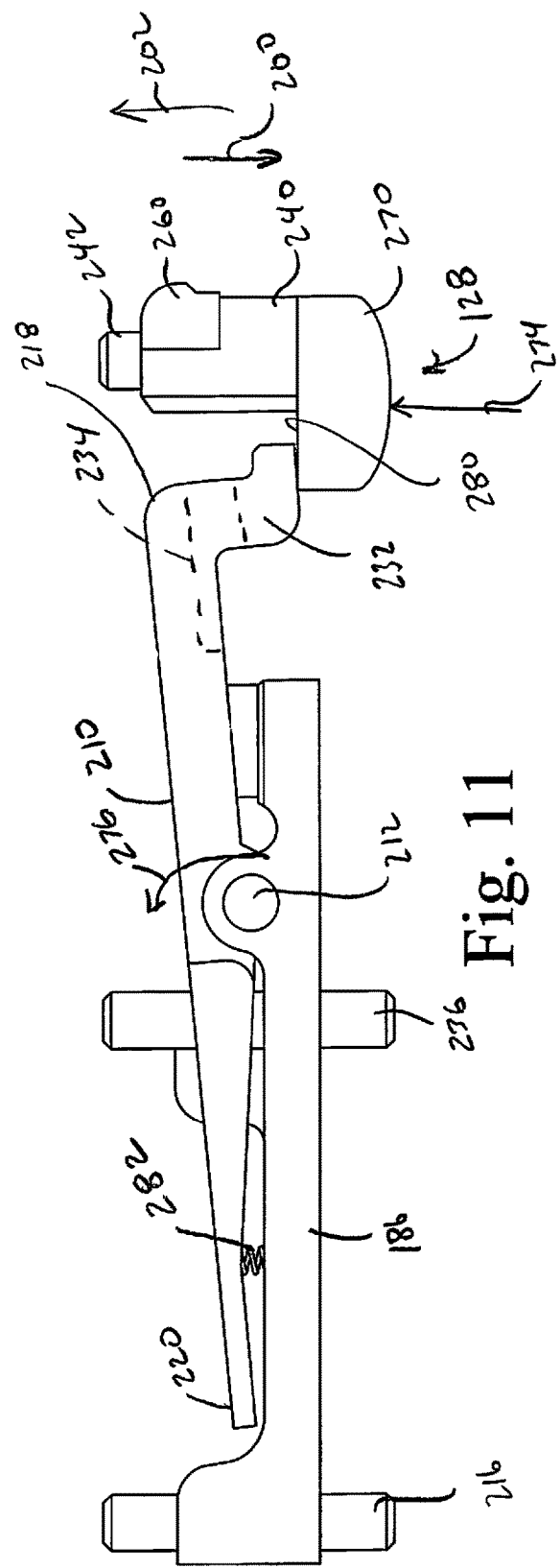
FIG. 11 is an elevation view of a locking assembly configured to secure the modular head component to the linkage housing.

As shown in FIG. 11, the legs 232 of the attachment link 210 engage a rear wall 280 of the button 270. The locking mechanism 128 also includes a biasing element 282 that is positioned between the distal end 220 of the attachment link 210 and the base link 186. In the illustrative embodiment, the biasing element 282 is a spring that is operable to bias the button 270 in the direction indicated by the arrow 200.

Figure 12:
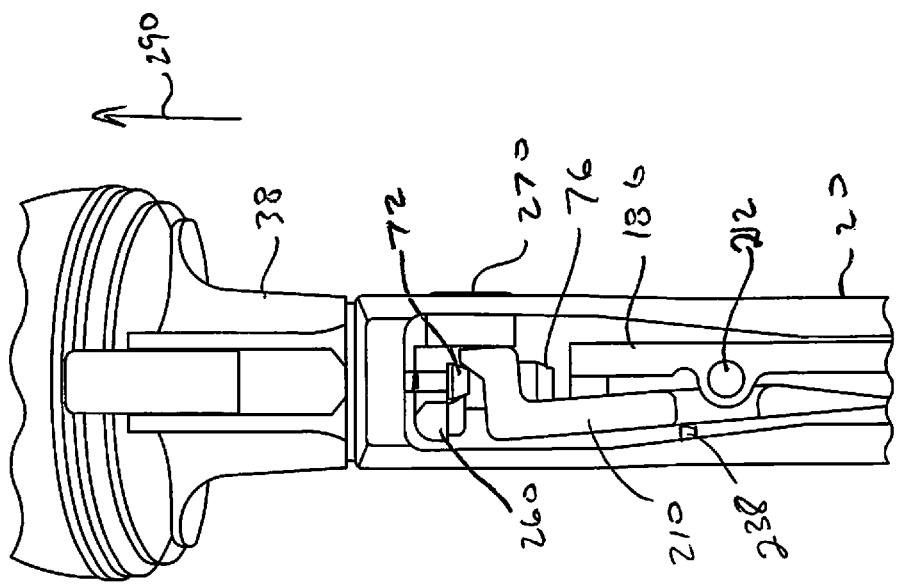
FIG. 12 is a plan view of the modular head component of FIG. 3 and the surgical instrument with the locking assembly in the closed configuration.
Figure 13:
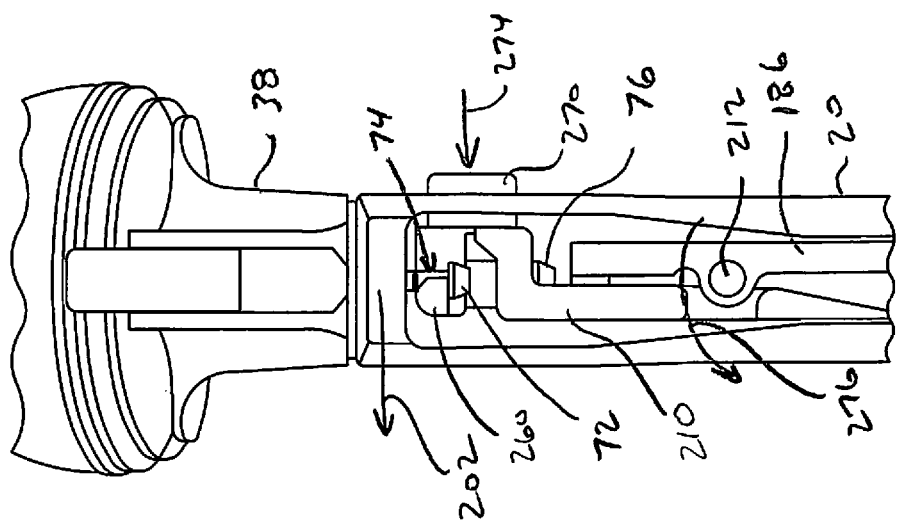
FIG. 13 is a plan view similar to FIG. 12 with the locking assembly in the open configuration.

The operation of the modular head locking mechanism 128 is shown in greater detail in FIGS. 12-13. As shown in FIG. 12, the flanges 260 are positioned in the grooves 74 and engaged with the proximal walls 75 of the stationary pins 72 of the modular head 38. The mounting legs 232 of the attachment link 210 are positioned in the groove 78 of the moveable pin 76 of the modular head 38 and thereby act to secure the modular head 38 to the handle 16. When force is applied in the direction indicated by the arrow 274 in FIG. 12, the bias exerted by the spring 282 is overcome and the attachment link 210 is rotated about the pin 212 in the direction indicated by the arrow 276, thereby permitting the bracket 240 to move in the direction indicated by the arrow 202. The flanges 260 advance out of contact with the stationary pins 72 and move into the position shown in FIG. 13 to free the stationary pins 72 for movement. Additionally, the mounting legs 232 are pivoted away from the moveable pin 76 to free moveable pin 76 for movement. With the locking mechanism 128 positioned as shown in FIG. 13, the user may detach the modular head 38 from the handle 16 by pulling in the direction indicated by arrow 290 in FIG. 13.

Figure 14:
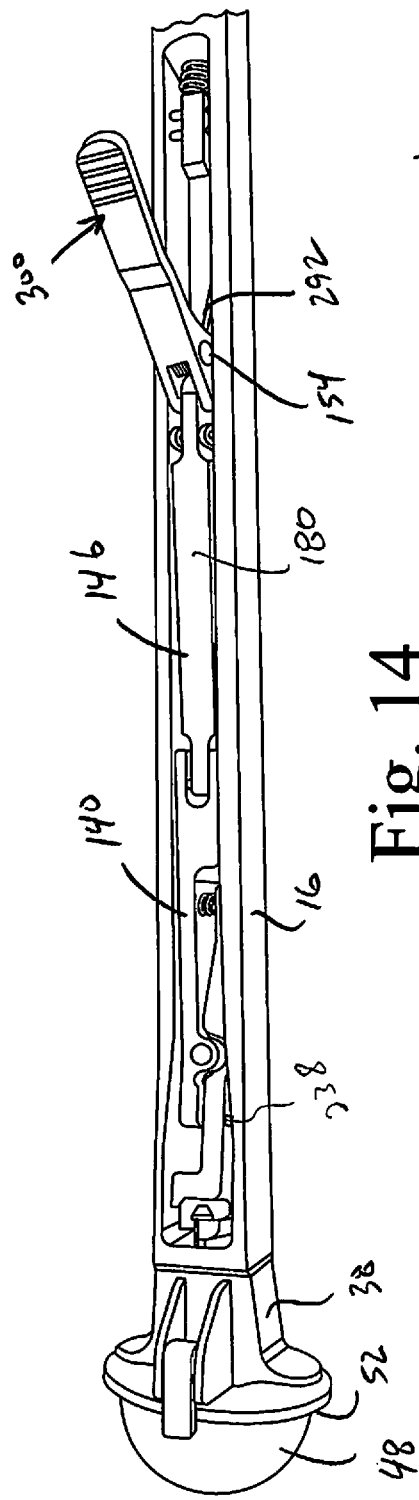
FIG. 14 is a perspective view of the surgical instrument of FIG. 1 with the lever in the open position.

Referring now to FIG. 14, the control lever 142 of the prosthetic component locking mechanism 130 is shown in the open position. In the illustrative embodiment, the prosthetic component locking mechanism 130 also includes a biasing element 292 that bias the control lever 142 in the open position. The biasing element 292 is illustratively a torsion spring. When the modular head 38 is attached to the handle 16 as shown in FIG. 14, a user may position an acetabular prosthetic component 40 over the cap 48 and engage the rim surface 57 of the component 40 with the rim surface 52 of the modular head 38. The user may apply a force to the control lever 142 in the direction indication by arrow 300 to cause the control lever 142 to pivot about the pin 154. As the control lever 142 pivots, the connecting link 146 is drawn distally as the main link 180 is pulled distally with the lever 142. The movement of the connecting link 146 pulls the proximal assembly 140 distally as well, thereby causing the mounting legs 232 of the attachment link 210 to exert a distal force on the wall 79 of the moveable pin 76 of the modular head 38 to pull back the pin 76.

As the moveable pin 76 is pulled by the attachment link 210, the locking arms 90 of the modular head 38 are rotated about pins 114 to advance the locking flanges 92 into the groove 58 of the prosthetic component 40, thereby securing the prosthetic component 40 to the instrument 10. Additionally, the stepped wall 238 of the pin 236 engages the wall 248 of the attachment link 210 to prevent actuation of the modular head locking mechanism 128 and removal of the head 38.

Figure 15:
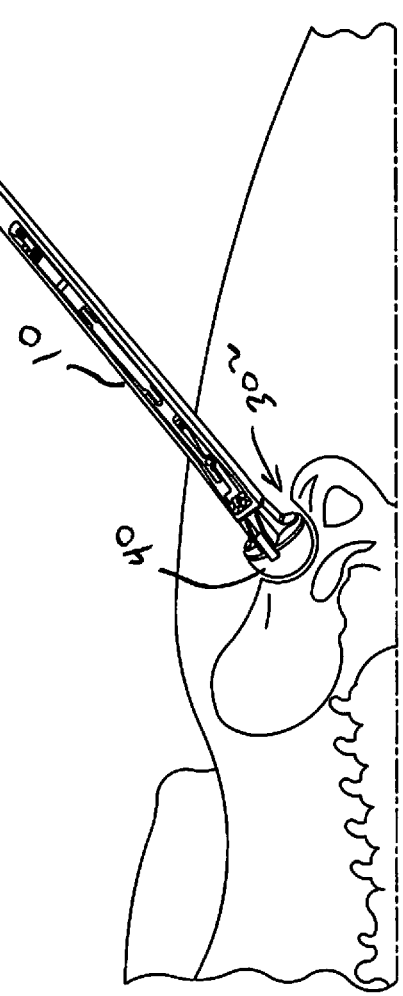
FIG. 15 is a perspective view of the surgical instrument of FIG. 1 positioned proximate to an acetabular cavity of a pelvis.

With the prosthetic component 40 secured to the instrument 10, the component 40 may be positioned in a patient's surgically-prepared acetabulum 302, as shown in FIG. 15. The user may then manipulate the instrument 10 to position the component 40 for implantation. The surgeon may grip the handle 16 and apply force to the impaction plate 18 with, for example, a mallet. The force applied to the impaction plate 18 drives the acetabular prosthetic component 40 into the acetabulum 302. The porous surface 54 on the acetabular prosthetic component 40 retains the acetabular prosthetic component 40 within the acetabular cavity.

The embodiments described above facilitate implanting an acetabular prosthetic component in an acetabular cavity of a patient. It will be appreciated that the surgical instruments and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A surgical instrument for implanting an acetabular prosthetic component comprising:
    a modular head comprising:
        a proximal end to retain the acetabular prosthetic component and an opposite distal end,
        a plurality of locking pins extending from the distal end of the modular head,
        a cap positioned at the proximal end of the modular head, the cap including a cap surface, and
        a locking arm extending from the proximal end of the modular head, the locking arm movable between an open position and a closed position, the locking arm positioned adjacent the cap, wherein in the open position the locking arm is spaced further from the cap than in the closed position; and
    a surgical handle extending distally from the modular head, the modular head being removably coupled to a proximal end of the surgical handle, the surgical handle comprising:
        a user-operated button having a body that engages a first of the plurality of locking pins of the modular head to lock the modular head to the surgical handle, and
        a linkage assembly engaging a second of the plurality of locking pins to actuate the locking arm.

2. The surgical instrument of claim 1, wherein the cap surface comprises a hemi-spherical outer surface sized to receive a hemi-spherical concave surface of the acetabular prosthetic component; and the cap further comprises a circular rim extending circumferentially around a distal end of the cap.

3. The surgical instrument of claim 2, wherein the locking arm further comprises a locking flange extending toward the hemi-spherical outer surface, the locking flange engaging a groove of the acetabular prosthetic component when the locking arm is in the closed position.

4. The surgical instrument of claim 1, wherein:
    each of the plurality of locking pins includes a groove formed therein; and
    the body of the user-operated button includes a bracket, the bracket engaging the groove formed in the first of the plurality of locking pins.

5. The surgical instrument of claim 4, wherein the user-operated button translates from a first side of the surgical handle toward a second side of the surgical handle to disengage the bracket of the body from the groove of the first of the plurality of locking pins to facilitate removing the modular head from the surgical handle.

6. The surgical instrument of claim 1, wherein:
    each of the plurality of locking pins includes a groove formed therein; and
    the linkage assembly includes an attachment link having a mounting leg, wherein the mounting leg of the attachment link engages the groove of the second of the plurality of locking pins.

7. The surgical instrument of claim 6, wherein the user-operated button translates from a first side of the surgical handle toward a second side of the surgical handle to pivot the attachment link so that the mounting leg of the attachment link disengages the groove of the second of the plurality of locking pins to facilitate removing the modular head from the surgical handle.

8. A surgical instrument for implanting an acetabular prosthetic component having a modular head comprising:
    a proximal end to retain the acetabular prosthetic component and an opposite distal end,
    a hemi-spherical outer surface positioned at the proximal end and sized to receive a hemi-spherical concave surface of the acetabular prosthetic component,
    a circular rim extending circumferentially around the distal end of the hemi-spherical outer surface,
    a stationary pin and a moveable pin extending from the distal end of the modular head, and
    a locking arm extending from the proximal end of the modular head, the locking arm hingedly coupled to the moveable pin, the moveable pin being moveable linearly in a first direction and a second direction to pivot the locking arm between an open position and a closed position, wherein in the open position the locking arm is spaced further from the hemi-spherical outer surface than in the closed position.

9. The surgical instrument of claim 8, further comprising a surgical handle extending distally from the modular head, the modular head being removably coupled to a proximal end of the surgical handle, the surgical handle comprising:
    a user-operated button having a body that engages the stationary pin of the modular head to lock the modular head to the surgical handle; and
    a linkage assembly engaging the moveable pin to actuate the locking arm, the linkage assembly extending a length of the surgical handle from the proximal end of the surgical handle to a distal end of the surgical handle, the linkage assembly including a lever at the distal end of the surgical handle, the lever actuated to move the locking arm.

10. The surgical instrument of claim 9 wherein:
    the stationary pin includes a groove formed therein, and the body of the user-operated button includes a bracket, the bracket engaging the groove formed in the stationary pin; and
    the moveable pin includes a groove formed therein, and the linkage assembly includes an attachment link having a mounting leg, wherein the mounting leg of the attachment link engages the groove of the moveable pin.

11. The surgical instrument of claim 10, wherein the user-operated button translates from a first side of the surgical handle toward a second side of the surgical handle to pivot the attachment link so that the mounting leg of the attachment link disengages the groove of the moveable pin to facilitate removing the modular head from the surgical handle.

12. The surgical instrument of claim 11, wherein the lever is actuated from a locked positioned to an unlocked position, wherein in the locked positioned the attachment link is translated distally to move the moveable pin distally, wherein in the unlocked position the attachment link is translated proximally to move the moveable pin proximally, wherein moving the moveable pin distally actuates the locking arm into the closed position, and moving the moveable pin proximally actuates the locking arm into the open position.

13. The surgical instrument of claim 12, wherein the surgical handle further comprises a lever release to retain the lever in the locked position, the lever release actuated to release the lever into the unlocked position, wherein the lever is positioned on a bottom of the surgical handle and rotates therefrom, and the lever release is positioned on a top of the surgical handle and translates distally and proximally along a length of the surgical handle, wherein translating the lever release distally releases the lever into the unlocked position.

14. The surgical instrument of claim 12, wherein positioning the lever in the locked position locks the user-operated button to lock the modular head to the surgical handle.

* * * * *